United States Patent [19]
Pucci et al.

[11] Patent Number: 5,250,156
[45] Date of Patent: Oct. 5, 1993

[54] METHOD OF SEPARATING ETHYL TERTIOBUTYL ETHER FROM MIXTURES WITH ETHANOL

[75] Inventors: Annick Pucci, Croissy Sur Senie; Paul Mikitenko, Noisy Le Roi; Massimo Zuliani, Rueil Malmaison, all of France

[73] Assignee: Institut Francais Du Petrole, Rueil Malmaison, France

[21] Appl. No.: 847,731

[22] Filed: Mar. 9, 1992

[30] Foreign Application Priority Data

Mar. 7, 1991 [FR] France .................. 91 02893

[51] Int. Cl.$^5$ .................. B01D 3/34; C07C 41/42
[52] U.S. Cl. .................. 203/39; 203/73; 203/74; 203/75; 203/76; 203/77; 203/92; 203/DIG. 6; 568/697; 568/699; 568/913
[58] Field of Search .................. 203/76, 75, 82, 83, 203/DIG. 6, 39, 73, 74, 92, 95, DIG. 9, 43–46; 568/697, 699, 913

[56] References Cited

U.S. PATENT DOCUMENTS

| | | |
|---|---|---|
| 2,721,222 | 10/1955 | Cottle et al. |
| 4,302,298 | 11/1981 | Mikitenko et al. .................. 568/699 |
| 4,324,924 | 4/1982 | Torck et al. .................. 568/699 |
| 4,440,963 | 4/1984 | Childs . |
| 4,808,270 | 2/1989 | Wernicke et al. .................. 568/699 |
| 5,015,783 | 5/1991 | Vora et al. .................. 568/697 |
| 5,122,236 | 6/1992 | Smith et al. .................. 568/697 |
| 5,158,652 | 10/1992 | Pucci et al. .................. 203/73 |

Primary Examiner—Wilbur Bascomb, Jr.
Attorney, Agent, or Firm—Millen, White, Zelano & Branigan

[57] ABSTRACT

The separation of ethyl tertiobutyl ether from mixtures with ethanol is based on heteroazeotropic distillation with water as the entrainer using two distillation columns, coupled with an overhead decanter. Purified ethanol is collected from the bottom of the first column and purified ETBE from the bottom of the second column. The separation method may be incorporated into an ETBE production unit in which isobutene (contained in a C$_4$-cut from steam cracking, catalytic cracking, or dehydrogenation of isobutane) is etherified by ethanol. Ethanol separated from the ETBE is then recycled to the etherification zone.

17 Claims, 1 Drawing Sheet

METHOD OF SEPARATING ETHYL TERTIOBUTYL ETHER FROM MIXTURES WITH ETHANOL

BACKGROUND OF THE INVENTION

The invention concerns the preparation of ethyl tertiobutyl ether (abbreviated to ETBE).

It is known that ethyl tertiobutyl ether, like methyl tertiobutyl ether (abbreviated to MTBE), may be used as an additive with a high octane number for lead-free petrols (opsolines) or petrols with a low lead content. The addition of ETBE to petrols may be envisaged, at concentrations, e.g.; up to about 15% by volume.

A method of preparing MTBE comprises carrying out a reaction in which methanol is added to isobutene, contained, e.g.) in a $C_4$ cut from steam cracking, catalytic cracking or dehydrogenation of isobutane. After the reaction, the residual methanol is generally hydrocarbons. This makes it fairly easy to obtain MTBE of a purity suitable for addition to petrols.

ETBE can be prepared by a similar process, with the methanol replaced by ethanol. Such a process is described, e.g., in "l'ETBE, un avenir pour l'ethanol (ETBE, a future for ethanol" by A. FORESTIERE, B. TORCK and G. PLUCHE, a paper read at the Conference on Biomass for Energy and Industry, Lisbon, 9-13 Oct. 1989 and in "MTBE/ETBE, an Incentive Flexibility for Refiners" by A. FORESTIERE et coll., a paper read at the Conference on Oxygenated Fuels in Europe, London, 22-23 May 1990.

In contrast with the MTBE process, however, when the $C_4$ hydrocarbons have been removed in this process, nearly all the residual ethanol is found to be mixed with the ETBE produced. The existence of an ethanol-ETBE azeotrope containing 21% by weight of ethanol at atmospheric pressure and boiling at 66.6° C. makes it difficult to separate ETBE of a purity sufficient to satisfy specifications on the ethanol content of petrols. Thus the ethanol content of ETBE must generally be from 5 to 10% by weight. ETBE will advantageously have to be purified to less than 2% by weight of ethanol in order to be conveyed to a refinery.

Thus there were great hopes of finding an economically attractive separating method, to enable ETBE to compete with MTBE as an additive to improve the octane number of lead-free petrols. This is what the invention proposes.

SUMMARY OF THE INVENTION

An object of the invention is therefore a method of separating ETBE from mixtures which it forms with ethanol, and more particularly from ETBE-ethanol mixtures emanating from the reaction of ethanol with a $C_4$ cut from steam cracking, catalytic cracking or dehydrogenation of isobutane.

Another object of the invention is a method of preparing ETBE including such a separating operation, wherein the ethanol is recycled to the etherification reactor.

The method of the invention for separating ETBE applies generally to mixtures which essentially comprise ethanol and ETBE in varying proportions, and more particularly to mixtures emanating from the reaction of adding ethanol to the isobutene contained in a $C_4$ cut from steam cracking, catalytic cracking or dehydrogenation of isobutane, generally containing 5 to 50% by weight of ethanol and more frequently 10 to 30%.

They may further contain very small proportions of other constituents, essentially dimers of isobutene, such as trimethylpentenes, tertiary butyl alcohol, diethylether and $C_5$ hydrocarbons; they may equally contain traces of ethers emanating from the addition of ethanol to $C_4$ olefins other than isobutene; in this description such ethers will not be distinguished from ETBE.

The method of the invention for separating ETBE, which is based on heteroazeotropic distillation with water as the entrainer, uses two columns coupled with an overhead decanter. The purified ethanol is collected at the bottom of the first column and the purified ETBE at the bottom of the, second one.

BRIEF DESCRIPTION OF THE DRAWING

The method of the invention is described below in connection with FIG. 1, where the schematic layout particularly shows the two columns (1 and 2), the decanter (8) and the lines connecting them.

DETAILED DESCRIPTION

Figure 1:
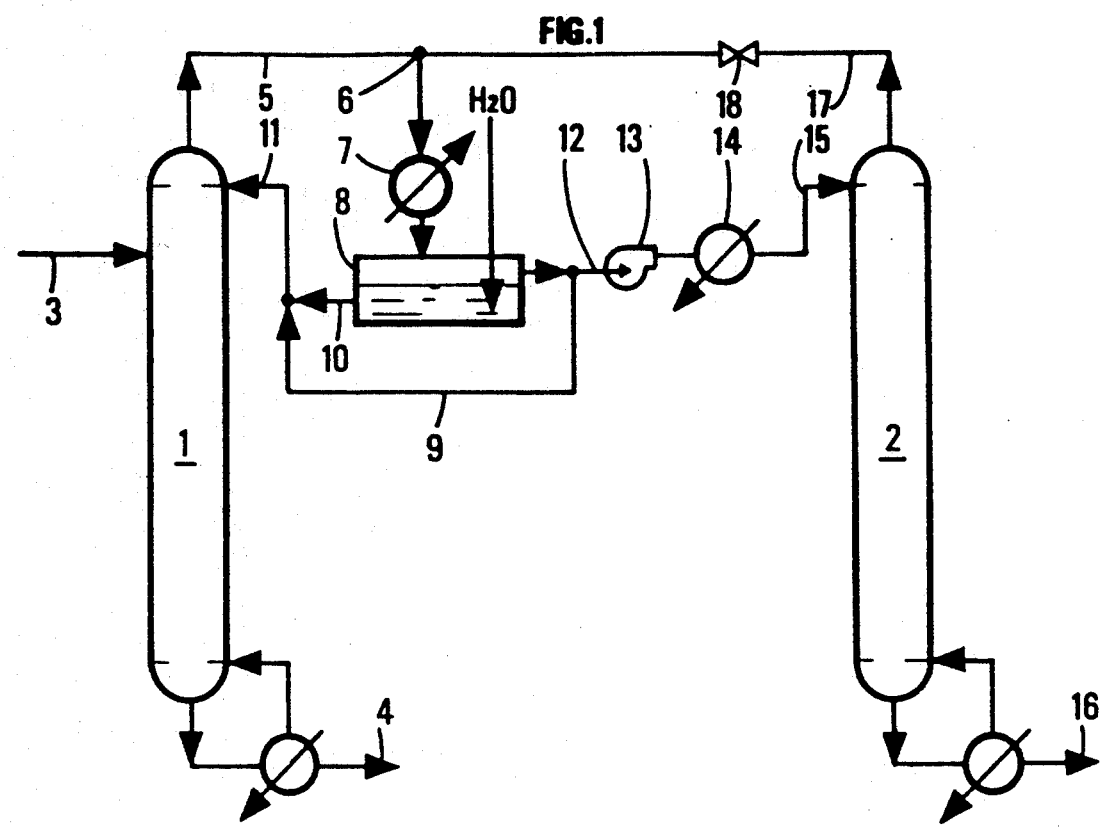

At least part of the water used in the method of the invention may be placed in the installation before it is started up, e.g., in the decanter. Any additional water required can then be fed in gradually in a transitional phase, until the conditions of equilibrium which characterize the steady state of the process have been established, as will be described below. The gradual introduction of water may be effected, e.g., at the decanter level.

The charge, comprising the mixture containing the ETBE and ethanol to be separated, is fed through a line 3 into the upper part of a first column 1, operating at a pressure p1, which is generally close to atmospheric and may, e.g., be from 0.05 to 0.2 MPa, and is heated to a bottom temperature of about 60 to 95° C. The temperature at which the charge is introduced may be from about 50° to 80° C.

The residue discharged at the bottom through a line 4 is purified ethanol.

The distillate is discharged at the top through a line 5 at a temperature close to that of the ternary azeotrope water/ethanol/ETBE at the pressure p1. Its composition is close to that of the azeotrope at the pressure p1; for example, for a pressure p1 of 0.1 MPa it is about 82.9% by weight of ETBE, about 11.6% by weight of ethanol and about 5.50% by weight of water. The distillate is mixed at 6 with the distillate from the second column, which has a reduced ETBE content, as will be described below. The mixture obtained is condensed in the condenser 7 and collected in the decanter 8, in which two phases are separated:

a lower phase containing a major proportion of water, a minor proportion of ethanol and a few percent of ETBE;

an upper phase containing a major proportion of ETBE, a minor proportion of ethanol and a few percent of water.

To enable a liquid reflux of a composition similar to that of the ternary azeotrope at the pressure p1 to be obtained at the top of column 1, a flow of upper phase (rich in ETBE) is brought out of the decanter 8 through a line 9, to which there is added a flow of lower aqueous phase which comes out of the decanter through a line 10. The discharge rates thereof are adjusted—allowing for the respective compositions of the two phases—so that the weight ratio of the discharge of aqueous phase to the discharge of ETBE phase is from 0.035 to 0.040. The streams are passed to the top of column 1, at 11, at a temperature of about 60° to 70° C.

Alternatively, the necessary reflux of part of the aqueous phase could be generated at the top of column 1, e.g., by a partial condenser inside the column, or it could be Produced by under-cooling the reflux of ETBE phase below its bubble point.

A second flow of upper phase rich in ETBE leaves the decanter 8 through a line 12. A pump 13 brings it to a pressure p2, which is in excess of the pressure p1 generally by a value Δp of about 0.4 to 1 MPa. The flow is heated in a heat exchanger 14 to a temperature of about 100° to 120° C., before being passed through a line 15 to the upper part of column 2. This operates at pressure p2 with a bottom temperature of about 120° to 150° C.

The fact that column 2 is operated at a pressure above that of column 1 particularly allows the boiling off rate from said column 2 to be reduced by a factor which may range from about 5 to 10. This is a considerable advantage from the economic point of view.

Moreover, it has been observed that operation of column 2 at too high a pressure involved a risk of the ETBE being thermally degraded when boiled off—apart from the disadvantage of making the products more difficult to separate. Hence the pressure p2 is not generally above 1 MPa and is most frequently about 0.5 MPa.

In order to obtain the desired pressure difference Δp, the stipulation of a pressure p1 below atmospheric may be envisaged. With this solution, however, a vacuum maintaining system would have to be installed in addition, which would not be advantageous from the economic point of view. The pressure p1 is therefore preferably from 0.1 to 0.2 MPa.

The residue from column 2 which is discharged through a line 16 at a temperature of about 100° to 120° C. essentially consists of purified ETBE.

The distillate discharged at the top through a line 17, with a depleted ETBE content, may, e.g., be made up of 72 to 76% by weight of ETBE, 18 to 20% by weight of ethanol and 5 to 7% by weight of water.

A pressure reducing valve 18 reduces its pressure to the pressure p1 of the distillate from column 1, with which it is mixed at 6. The mixture of distillates is then condensed at 7 and collected in the decanter 8 as already described above.

Under the operating conditions mentioned in the preceding description, the ethanol at the bottom of column 1 and the ETBE at the bottom of column 2 may be obtained with a high degree of purity, e.g., over 98% by weight for ethanol and 99.99% by weight for ETBE.

Losses of water which may be incurred while the process is being carried out (in the form of traces of water which may come out with the ethanol and/or ethyl tertiobutyl ether) may be compensated for by adding water, e.g., periodically, for instance, at the decanter level.

The invention also proposes a method of preparing ETBE by etherifying isobutene contained in a $C^4$ cut from steam cracking, catalytic cracking or deshydrogenation of isobutane, by means of ethanol.

Figure 2:
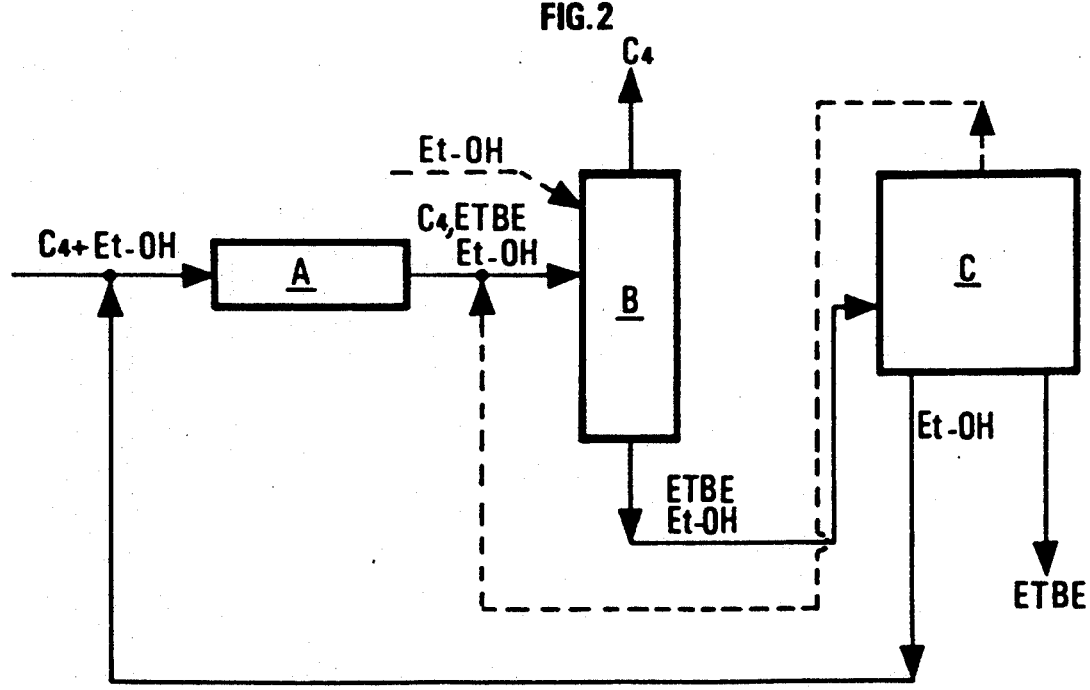
FIG. 2 is a schematic flowsheet illustrating the application of the invention to an integrated process for the production of ETBE.

The method of preparing ETBE, which will be described in connection with the layout in FIG. 2 of the accompanying drawings, then includes the following stages: in a zone A, putting ethanol into contact with a $C^4$ cut from steam cracking, catalytic cracking or dehydrogenation of isobutane, under reaction conditions; the product leaving reaction zone A chiefly contains ETBE, ethanol, $C^4$ hydrocarbons o&her than isobutene and non-reacted isobutene. This product is passed into a distillation zone B, where the $C^4$ hydrocarbons with a much depleted isobutene content are separated at the top and a mixture of ETBE and ethanol at the bottom. If more complete elimination of isobutene is required reactive distillation B', with replenishment of ethanol as indicated in broken lines in FIG. 2, may be carried out instead of a single distillation B. The mixture of ETBE and ethanol, collected at the bottom of zone B, is in all cases passed into a zone C, where the separating method of the invention is carried out.

From zone C the purified ethanol collected is advantageously recycled as a replenishment to reaction zone A and/or reactive distillation zone B'.

The following example is given to illustrate the invention.

EXAMPLE

The charge to be treated contains 80% by weight of ETBE and 20% by weight of ethanol.

The following apparatus is used:

a first stainless steel distillation column 50 mm in diameter and comprising 38 perforated trays with a weir, spaced 5 cm apart;

a second stainless steel distillation column 50 mm in diameter and comprising 15 perforated trays with a weir, spaced 5 cm apart; and a 0.5 liter decanter.

It is laid out as indicated in the diagram in the accompanying figure.

0.100 kg of water is first placed in the decanter.

The charge is placed in the first column at the second tray level (with the trays being counted upwards).

The first column is heated to a bottom temperature of 78° C. and the second to a bottom temperature of 135° C.

During the start up period water is introduced gradually at the decanter level until the equilibria which characterize the steady state are established. The conditions for this state are set out in the following table.

TABLE

|  | Column 1 | Column 2 |
| --- | --- | --- |
| Pressure (MPa) | 0.1 | 0.5 |
| Feed |  |  |
| Flow rate (kg/h) | 1.50 | 4.47 |
| Temperature (°C.) | 67 | 113 |
| Distillate |  |  |
| Flow rate (kg/h) | 5.78 | 3.28 |
| Temperature (°C.) | 64 | 114 |
| Product |  |  |
| Flow rate (kg/h) | 0.30 | 1.20 |
| Temperature (°C.) | 77.5 | 64 |
| Purity (% wt) | Ethanol 98.6 | ETBE >99.9 |

The two distillates are combined and the mixture thereof is condensed then passed to the decanter (flow rate of liquid at inlet: 9.06 kg/h).

From the decanter a reflux is passed to the first column, tray no. 1 at 65° C. (total flow rate: 4.58 kg/h). The reflux results from combining an upper phase flow (flow rate: 4.42 kg/h) with a lower phase flow (flow rate: 0.16 kg/h) from the decanter.

A further stream of upper phase is passed out of the decanter and brought to 0.5 MPa and 113° C. to feed column 2 at the level of tray no. 1.

The flow rate, temperature and purity of the products are indicated in the above table.

We claim:

1. A method of separating ethyl tertiobutyl ether from mixtures which it forms with ethanol, wherein a charge chiefly comprising ethyl tertiobutyl ether (ETBE) and ethanol is treated continuously in an installation comprising two distillation columns connected overhead to a decanter; the charge is introduced at a temperature of about 50° to 80° C. into the upper part of the first column, which operates at a pressure p1 of 0.05 to 0.2 MPa, said first column being heated to a bottom temperature of about 60° to 95° C.; distillate from the first column is mixed with distillate from the second column and the mixture thus formed is condensed; the condensate obtained is decanted into a lower phase with a major proportion of water and a minor proportion of ethanol, and an upper phase with a major proportion of ethyl tertiobutyl ether and a minor proportion of ethanol; a liquid reflux of a composition close to that of a ternary azeotrope at pressure p1 is produced at the top of the first column at a temperature of about 60° to 70° C., by passing appropriate proportions of a first stream of upper phase and of a stream of lower phase to the top of the first column at a temperature of about 60° to 70° C.; a second stream of upper phase, brought to a pressure p2, which is higher than pressure p1 by a value Δp of 0.4 to 1 MPa, and heated to a temperature of about 100° to 120° C., is fed to the upper part of the second column, which operates at pressure p2 and which is heated to a bottom temperature of about 120° to 150° C.; the distillate from the second column is depressurized to pressure p1 then mixed with the distillate from the first column; and purified ethanol is collected from the bottom of the first column and purified ethyl tertiobutyl ether from the bottom of the second column.

2. The method of claim 1, wherein the charge includes 5 to 50% by weight of ethanol.

3. The method of claim 1, wherein the charge includes 10 to 30% by weight of ethanol.

4. The method of claim 1 wherein the pressure p1 is approximately 0.1 to 0.2 MPa, and the pressure p2 is 1 MPa at the maximum.

5. The method of claim 1 wherein in the stream of lower phase and the first stream of upper phase from the decanter are in a weight ratio ranging from 0.035 to 0.040.

6. The method of claim 1 wherein in the charge emanates from preparation of the ETBE through etherification with ethanol of isobutene contained in a C4 cut from steam cracking, catalytic cracking or dehydrogenation of isobutane.

7. The method of claim 6, wherein the charge contains about 80% by weight of ETBE and about 20% by weight of ethanol.

8. A method of preparing ethyl tertiobutyl ether (ETBE) through etherification with ethanol of isobutene contained in a C4 cut from steam cracking, catalytic cracking or dehydrogenation of isobutane, wherein, in a reaction zone A, ethanol and the C4 cut are put into contact under reaction conditions; the product discharged from the reaction zone A, chiefly containing ETBE, ethanol, C4-hydrocarbons other than isobutene, and non-reacted isobutene, is passed into a distillation zone B, where the C4-hydrocarbons including non-reacted isobutene are separated at the top and a mixture of ETBE and ethanol at the bottom; and said mixture is passed into a separating zone C; and wherein in said separating zone C, said mixture of ETBE and ethanol is treated continuously in an installation comprising two distillation columns connected overhead to a decanter; said mixture is introduced at a temperature of about 50°-80° C. into the upper part of the first column, which operates at a pressure p1 of 0.05 to 0.2 MPa, column, which operates at a pressure p1 of 0.05 to 0.2 MPa, said first column being heated to a bottom temperature of about 60°-95° C.; distillate from the first column is mixed with distillate from the second column and the mixture thus formed is condensed; the condensate obtained is decanted into a lower phase with a major proportion of water and a minor proportion of ethanol, and an upper phase with a major proportion of ETBE and a minor proportion of ethanol; a liquid reflux of a composition of substantially that of a ternary azeotrope of ETBE, ethanol, and water at pressure p1 is produced at the top of the first column at a temperature of about 60°-70° C., by passing sufficient proportions of a first stream of upper phase and of a stream of lower phase to the top of the first column at a temperature of about 60°-70° C.; a second stream of upper phase, brought to a pressure p2, which is higher than pressure p1 by a value Δp of 0.4 to 1 MPa, and heated to a temperature of about 100°-120° C., is fed to the upper part of the second column, which operates at pressure p2 and which is heated to a bottom temperature of about 120°-150° C.; the distillate from the second column is depressurized to pressure p1, then mixed with the distillate from the first column; and purified ethanol is collected from the bottom of the first column and purified ETBE from the bottom of the second column.

9. The method of claim 8 wherein the purified ethanol from the separating zone C is recycled to the inlet of the reaction zone A.

10. The method of claim 3, wherein the pressure p1 is approximately 0.1 to 0.2 MPa, and the pressure p2 is 1 MPa at the maximum.

11. The method of claim 3, wherein the stream of lower phase and the first stream of upper phase from the decanter are in a weight ratio ranging from 0.035 to 0.040.

12. The method of claim 4, wherein the stream of lower phase and the first stream of upper phase from the decanter are in a weight ratio ranging from 0.035 to 0.040.

13. A method of preparing ethyl tertiobutyl ether (ETBE) through etherification with ethanol of isobutene contained in a C4 cut from steam cracking, catalytic cracking or dehydrogenation of isobutane, wherein, in a reaction zone A, ethanol and the C4 cut are put into contact under reaction conditions; the product discharged from the reaction zone A, chiefly containing ETBE, ethanol, C4-hydrocarbons other than isobutene, and non-reacted isobutene, is passed into a reactive distillation zone B', passing additional ethanol into said reactive distillation zone B' to remove the non-reacted isobutene, separating the C4-hydrocarbons at the top of the reactive distillation zone B', and separating a mixture of ETBE and ethanol at the bottom of the reactive distillation zone B'; and said mixture is passed into a separating zone C; and wherein in said separating zone C, said mixture of ETBE and ethanol is treated continuously in an installation comprising two distillation columns connected overhead to a decanter; said mixture is introduced at a temperature of about 50°-80° C. into the upper part of the first column, which operates at a pressure p1 of 0.05 to 0.2 MPa, said first column being heated to a bottom temperature of about 60°-95° C.; distillate from the first column is mixed with distillate from the second column and the mixture thus formed is condensed; the condensate obtained is decanted into a lower phase with a major proportion of water and a minor proportion of ethanol, and an upper phase with a major proportion of ETBE and a minor proportion of ethanol; a liquid reflux of a composition of substantially that of a ternary azeotrope of ETBE, ethanol, and water at pressure p1 is produced at the top of the first column at a temperature of about 60°-70° C., by passing sufficient proportions of a first stream of upper phase and of a stream of lower phase to the top of the first column at a temperature of about 60°-70° C.; a second stream of upper phase, brought to a pressure p2, which is higher than pressure p1 by a value $\Delta p$ of 0.4 to 1 MPa, and heated to a temperature of about 100°-120° C., is fed to the upper part of the second column, which operates at pressure p2 and which is heated to a bottom temperature of about 120°-150° C.; the distillate from the second column is depressurized to pressure p1, then mixed with the distillate from the first column; and purified ethanol is collected from the bottom of the first column and purified ETBE from the bottom of the second column.

14. The method of claim 13, wherein the purified ethanol from the separating zone C is recycled to the distillation zone B'.

15. The method of claim 1, wherein sufficient water is introduced into the installation to achieve steady-state operation.

16. The method of claim 8, wherein sufficient water is introduced into the installation to achieve steady-state operation.

17. The method of claim 13, wherein sufficient water is introduced into the installation to achieve steady-state operation.

* * * * *